United States Patent
Chen et al.

(12) 
(10) Patent No.: US 6,576,756 B2
(45) Date of Patent: Jun. 10, 2003

(54) ISOLATED NUCLEIC ACID MOLECULE ENCODING CANCER ASSOCIATED ANTIGEN, THE ANTIGEN ITSELF, AND USES THEREOF

(75) Inventors: Yao-Tseng Chen, New York, NY (US); Ali Gure, New York, NY (US); Solam Tsang, New York, NY (US); Elisabeth Stockert, New York, NY (US); Elke Jäger, Frankfurt am Main (DE); Knuth Alexander, Frankfurt am Main (DE); Lloyd J. Old, New York, NY (US)

(73) Assignees: Ludwig Institute for Cancer Research, New York, NY (US); Cornell Research Foundation, Inc., Ithaca, NY (US); Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 09/899,651

(22) Filed: Jul. 6, 2001

(65) Prior Publication Data

US 2002/0111470 A1 Aug. 15, 2002

Related U.S. Application Data

(62) Division of application No. 09/061,709, filed on Apr. 17, 1998, now Pat. No. 6,297,364.

(51) Int. Cl.[7] .......................... C07H 21/04; C07K 1/00; A01N 37/18

(52) U.S. Cl. ............................ 536/23.5; 530/350; 514/2
(58) Field of Search .............................. 530/350; 514/2; 536/23.5

(56) References Cited

U.S. PATENT DOCUMENTS 5,997,872 A * 12/1999 Lucas et al. ............. 424/185.1

OTHER PUBLICATIONS

Alberts et al. (Molecular Biology of the Cell, 3rd edition, 1994, p. 465).*
Fu et al. (EMBO Journal, 1996, vol. 15, pp. 4392–4401).*
Rama et al. (Biochem. J. vol. 318, 1996, pp. 333–341).*
Gura (Science, v278, 1997, pp. 1041–1042).*
Bellone et al. (Immunology Today, v20 (10), 1999, pp. 457–462).*
Gaiger et al. (Blood, vol. 96, No. 4, Aug. 2000, pp. 1480–1489).*
De Plaen et al. (SwissProtein Database, Accession No. P43363, Immunogenetics, vol. 40, 1994).*

* cited by examiner

Primary Examiner—Anthony C. Caputa
Assistant Examiner—Gary B. Nickol
(74) Attorney, Agent, or Firm—Fulbright & Jaworski L.L.P.

(57) ABSTRACT

The invention relates to the isolation of a nucleic acid molecule which encodes a cancer associated antigen. Also a part of the invention is the antigen itself, and the uses of the nucleic acid molecule and the antigen, and peptides derived from it.

3 Claims, No Drawings

US 6,576,756 B2

ISOLATED NUCLEIC ACID MOLECULE ENCODING CANCER ASSOCIATED ANTIGEN, THE ANTIGEN ITSELF, AND USES THEREOF

RELATED APPLICATION

This application is a divisional application of Ser. No. 09/061,709, filed Apr. 17, 1998, now U.S. Pat. No. 6,297, 364.

FIELD OF THE INVENTION

This invention relates to an antigen associated with cancer, the nucleic acid molecule encoding it, as well as the uses of these.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

Two basic strategies have been employed for the detection of such antigens, in e.g., human tumors. These will be referred to as the genetic approach and the biochemical approach. The genetic approach is exemplified by, e.g., dePlaen et al., Proc. Natl. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines which are tested for the expression of the specific antigen. The biochemical approach, exemplified by, e.g., O. Mandelboim, et al., Nature 369: 69 (1994) incorporated by reference, is based on acidic elution of peptides which have bound to MHC-class I molecules of tumor cells, followed by reversed-phase high performance liquid chromatography (HPLC).

Antigenic peptides are identified after they bind to empty MHC-class I molecules of mutant cell lines, defective in antigen processing, and induce specific reactions with cytotoxic T-lymphocytes. These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; and second, they depend on the establishment of cytotoxic T cell lines (CTLs) with predefined specificity.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Brichard et al. J. Exp. Med. 178: 489–495 (1993); Coulie, et al., J. Exp. Med. 180: 35–42 (1994); Kawakami, et al., Proc. Natl. Acad. Sci. USA 91: 3515–3519 (1994).

Further, the methodologies described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., Proc. Natl. Acad. Sci. USA 92: 11810–11913 (1995), incorporated by reference. Also, see U.S. Pat. No. 5,698,396, and application Ser. No. 08/479,328, filed on Jun. 7, 1995 and Jan. 3, 1996, respectively. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J 144: 2333–2340 (1995)

This methodology has been applied to a range of tumor types, including those described by Sahin et al., supra, and Pfreundschuh, supra, as well as to esophogeal caner (Chen et al., Proc. Natl. Acad. Sci. USA 94: 1914–1918 (1997)); lung cancer (Güre et al., Cancer Res. 58: 1034–1041 (198)); colon cancer (Ser. No. 08/948,705 filed Oct. 10, 1997) incorporated by reference, and so forth. Among the antigens identified via SEREX are the SSX2 molecule (Sahin et al., Proc. Natl. Acad. Sci. USA 92: 11810–11813 (1995); Tureci et al., Cancer Res. 56: 4766–4772 (1996); NY-ESO-1 Chen, et al., Proc. Natl. Acad. Sci. USA 94: 1914–1918 (1997); and SCP1 (Ser. No. 08/892,705 filed Jul. 15, 1997) incorporated by reference. Analysis of SEREX identified antigens has shown overlap between SEREX defined and CTL defined antigens. MAGE-1, tyrosinase, and NY-ESO-1 have all been shown to be recognized by patient antibodies as well as CTLs, showing that humoral and cell mediated responses do act in concert.

It is clear from this summary that identification of relevant antigens via SEREX is a desirable aim. The inventors have modified standard SEREX protocols and have screened a cell line known to be a good source of the antigens listed supra, using allogeneic patient sample. A new antigen has been identified in this way, and has been studied. The antigen, referred to hereafter as "CT7", is one aspect to the invention, which is discussed in the Detailed Description which follows.

DETAILED DESCRIPTION

EXAMPLE 1

The melanoma cell referred to as SK-MEL-37 was used, because it has been shown to express a number of members of the CT antigen family, including MAGE-1 (Chen et al., Proc. Natl. Acad. Sci USA 91: 1004–1008 (1994); NY-ESO-1 (Chen et al. Proc. Natl. Acad. Sci. USA 94: 1914–1918 (1997)); and various members of the SSX family (Gure et al., Int. J. Cancer 72: 965–971 (1997)).

Total RNA was extracted from cultured samples of SK-MEL-37 using standard methods, and this was then used to construct a cDNA library in commercially available, λZAP expression vector, following protocols provided by the manufacturer. The cDNA was then transfected into *E. coli* and screened, following Sahin et al., Proc. Natl. Acad. Sci. USA 92: 11810–11813 (1995), incorporated by reference, and Pfreundschuh, U.S. Pat. No. 5,698,396, also incorporated by reference. The screening was done with allogeneic patient serum "NW38". This serum had been shown, previously, to contain high titer antibodies against MAGE-1 and NY-ESO-1. See, e.g., Jäger et al., J. Exp. Med. 187: 265–270 (1998), incorporated by reference. In brief, serum was diluted 1:10, preabsorbed with lysates of transfected *E. coli*, further diluted to 1:2000, and then incubated overnight at room temperature with nitrocellulose membranes containing phage plaques, prepared in accordance with Sahin et al., and Pfreundschuh, supra. The library contained a total of $2.3 \times 10^7$ primary clones. After washing, the filters were incubated with alkaline phosphatase conjugated, goat anti-human Fcγ secondary antibodies, and were then visualized by incubating with 5-bromo-4-chloro-3-indolyl phosphate, and nitroblue tetrazolium.

After screening $1.5 \times 10^5$ of the clones, a total of sixty-one positives had been identified. Given this number, screening was stopped, and the positive clones were subjected to further analysis.

EXAMPLE 2

The positive clones identified in example 1, supra, were purified, the inserts were excised in vitro, and inserted into a commercially available plasmid, pBK-CMV, and then evaluated on the basis of restriction mapping with EcoRI and XbaI. Clones which represented different inserts on the basis of this step were sequenced, using standard methodologies.

There was a group of 10 clones, which could not be classified other than as "miscellaneous genes", in that they did not seem to belong to any particular family. They consisted of 9 distinct genes, of which four were known, and five were new. The fifty one remaining clones were classified into four groups. The data are presented in Tables 1 and 2, which follow.

The largest group are genes related to KOC ("KH-domain containing gene, overexpressed in cancer which has been shown to be overexpressed in pancreatic cancer, and maps to chromosome 7p11.5. See Müeller-Pillasch et al., Oncogene 14: 2729–2733 (1997). Two of the 33 were derived from the KOC gene, and the other 31 were derived from two previously unidentified, but related genes.

Eleven clones, i.e., Group 2, were MAGE sequences. Four were derived from MAGE-4a, taught by DePlaen et al, Immunogenetics 40: 360–369, Genbank U10687, while the other 7 hybridized to a MAGE-4a probe, derived from the 5' sequence, suggesting they belong to the MAGE family.

The third group consisted of five clones of the NY-ESO-1 family. Two were identical to the gene described by Chen et al., Proc. Natl. Acad. Sci. USA 94: 1914–1918 (1997), and in Ser. No. 08/725,182, filed Oct. 3, 1996, incorporated by reference. The other three were derived from a second member of the NY-ESO-1 family, i.e., LAGE-1. See U.S. application Ser. No. 08/791,495, filed Jan. 27, 1997 and incorporated by reference.

The fourth, and final group, which is the subject of the invention, related to a novel gene referred to as CT7. This gene, the sequence of which is presented as SEQ ID NO: 1, was studied further.

TABLE 1

SEREX-identified genes from allogeneic screening of SK-MEL-37 library

| Gene group | # of clones | Comments |
|---|---|---|
| KOC | 33 | derived from 3 related genes |
| MAGE | 11 | predomiantly MAGE-4a (see text) |
| NY-ESO-1 | 5 | derived from 2 related genes (NY-ESO-1, LAGE-1) |
| CT7 | 2 | new cancer/testis antigen |
| Miscellaneous | 10 | see Table 2 |

TABLE 2

SEREX-identified genes from allogeneic screening of SK-MEL-37 library--Miscellaneous group

| Clone designation | Gene |
|---|---|
| MNW-4, MNW-7 | S-adenyl homocysteine hydrolase |
| MNW-6a | Glutathione synthetase |
| MNW-24 | proliferation-associated protein p38-2G4 |
| MNW-27a | phosphoribosyl pyrophophate synthetase-associated protein 39 |
| MNW-6b | unknown gene, identical to scquence tags from pancreas, uterus etc. |
| MNW-14b | unknown gene, identical to sequence tags from lung, brain, fibroblast etc. |
| MNW-34a | unknown gene, identical to sequence tags from multiple tissues |
| MNW-17 | unknown gene, identical to sequences tags from pancreas and fetus |
| MNW-29a | unknown gene, no significant sequence homology, universally expressed |

EXAMPLE 3

The two clones for CT7, referred to supra, were 2184 and 1965 base pairs long. Analysis of the longer one was carried out. It presented an open reading frame of 543 amino acids, which extended to the 5' end of the sequence, indicating that it was a partial cDNA clone.

In order to identify the complete sequence, and to try to identify additional, related genes, a human testicular cDNA library was prepared, following standard methods, and screened with probes derived from the longer sequence, following standard methods.

Eleven positives were detected, and sequenced, and it was found that all derived from the same gene. When the polyA tail was excluded, full length transcript, as per SEQ ID NO: 1, consisted of 4265 nucleotides, broken down into 286 base pairs of untranslated 5'-region, a coding region of 3429 base pairs, and 550 base pairs of untranslated 3' region. The predicted protein is 1142 amino acids long, and has a calculated molecular mass of about 125 kilodaltons. See SEQ ID NO: 2.

The nucleic acid and deduced amino acid sequences were screened against known databases, and there was some homology with the MAGE-10 gene, described by DePlaen et al., Immunogenetics 40: 360–369 (1994). The homology was limited to about 210 carboxy terminal amino acids, i.e., amino acids 908–1115 of the subject sequence, and 134–342 of MAGE-10. The percent homology was 56%, rising to 75% when conservative changes are included.

There was also extensive homology with a sequence reported by Lucas et al., Canc. Res. 58: 743–752 (1998), and application Ser. No. 08/845,528 filed Apr. 25, 1997, also incorporated by reference. A total of 14 nucleotides differ in the open reading frame, resulting in a total of 11 amino acids which differ between the sequences.

The 5' region of the nucleotide and sequence and corresponding amino acid sequence demonstrates a strikingly repetitive pattern, with repeats rich in serine proline, glutamine, and leucine, with an almost invariable core of PQSPLQI (SEQ ID NO: 3) In the middle of the molecule, 11 almost exact repeats of 35 amino acids were observed. The repetitive portions make up about 70% of the entire sequence, begin shortly after translation initiation, at position 15, and ending shortly before the region homologous to MAGE 4a.

EXAMPLE 4

The expression pattern for mRNA of CT7 was then studied, in both normal and malignant tissues. RT-PCR was used, employing primers specific for the gene. The estimated melting temperature of the primers was 65–70° C., and they were designed to amplify 300–600 base pair segments. A total of 35 amplification cycles were carried out, at an annealing temperature of 60° C. Table 3, which follows, presents the data for human tumor tissues. CT7 was expressed in a number of different samples. Of fourteen normal tissues tested, there was strong expression in testis, and none in colon, brain, adrenal, lung, breast, pancreas, prostate, thymus or uterus tissue.

There was low level expression in liver, kidney, placenta and fetal brain with fetal brain showing three transcripts of different size. The level of expression was at least 20–50 times lower than in testis. Melanoma cell lines were also screened. Of these 7 of the 10 tested showed strong expression, and one showed weak expression.

TABLE 3

CT7 mRNA expression in various human tumors by RT-PCR

| Tumor type | mRNA, positive/total |
|---|---|
| Melanoma | 7/10 |
| Breast cancer | 3/10 |
| Lung cancer | 3/9 |
| Head/neck cancer | 5/14 |
| Bladder cancer | 4/9 |
| Colon cancer | 1/10 |
| Leimyosarcoma | 1/4 |
| synovial sarcoma | 2/4 |
| Total | 26/70 |

EXAMPLE 5

Southern blotting experiments were then carried out to determine if if CT7 belonged to a family of genes. In these experiments, genomic DNA was extracted from normal human tissues. It was digested with BamHI, EcoRI, and HindIII, separated on a 0.7% agarose gel, blotted onto a nitrocellulose filter, and hybridized, at high stringency (65° C., aqueous buffer), with a $^{32}$P labelled probe, derived from SEQ ID NO: 1.

The blotting showed anywhere from two to four bands, suggesting one or two genes in the family.

The foregoing examples describe the isolation of a nucleic acid molecule which encodes a cancer associated antigen. "Associated" is used herein because while it is clear that the relevant molecule was expressed by several types of cancer, other cancers, not screened herein, may also express the antigen.

The invention relates to those nucleic acid molecules which encode the antigen CT7 as described herein, such as a nucleic acid molecule consisting of the nucleotide sequence SEQ ID NO: 1. Also embraced are those molecules which are not identical to SEQ ID NO: 1, but which encode the same antigen.

Also a part of the invention are expression vectors which incorporate the nucleic acid molecules of the invention, in operable linkage (i.e., "operably linked") to a promoter. Construction of such vectors, such as viral (e.g., adenovirus or vaccinia virus) mutated or attenuated viral vectors is well within the skill of the art, as is the transformation or transfection of cells, to produce eukaryotic cell lines, or prokaryotic cell strains which encode the molecule of interest. Exemplary of the host cells which can be employed in this fashion are COS cells, CHO cells, yeast cells, insect cells (e.g., *Spodoptera frugiperda*), NIH 3T3 cells, and so forth. Prokaryotic cells, such as *E. coli* and other bacteria may also be used. Any of these cells can also be transformed or transfected with further nucleic acid molecules, such as those encoding cytokines, e.g., interleukins such as IL-2, 4, 6, or 12 or HLA or MHC molecules.

Also a part of the invention is the antigen described herein, both in original form and in any different post translational modified form. The molecule is large enough to be antigenic without any posttranslational modification, and hence it is useful as an immunogen, when combined with an adjuvant (or without it), in both precursor and post-translationally modified forms. Antibodies produced using this antigen, both poly and monoclonal, are also a part of the invention as well as hybridomas which make monoclonal antibodies to the antigen. The whole protein can be used therapeutically, or in portions, as discussed infra. Also a part of the invention are antibodies against this antigen, be these polyclonal, monoclonal, reactive fragments, such as Fab, F(ab)$_2$' and other fragments, as well as chimeras, humanized antibodies, recombinantly produced antibodies, and so forth.

As is clear from the disclosure, one may use the proteins and nucleic acid molecules of the invention diagnostically. The SEREX methodology discussed herein is premised on an immune response to a pathology associated antigen. Hence, one may assay for the relevant pathology via, e.g., testing a body fluid sample of a subject, such as serum, for reactivity with the antigen per se. Reactivity would be deemed indicative of possible presence of the pathology so, too, could one assay for the expression of the antigen via any of the standard nucleic acid hybridization assays which are well known to the art, and need not be elaborated upon herein. One could assay for antibodies against the subject molecule, using standard immunoassays as well.

Analysis of SEQ ID NO: 1 will show that there are 5' and 3' non-coding regions presented therein. The invention relates to those isolated nucleic acid molecules which contain at least the coding segment, i.e., nucleotides 54–593, and which may contain any or all of the non-coding 5' and 3' portions.

As was discussed supra, study of other members of the "CT" family reveals that these are also processed to peptides which provoke lysis by cytolytic T cells. There has been a great deal of work in motifs for various MHC or HLA molecules, which is applicable here. Hence, a further aspect of the invention is a therapeutic method, wherein one or more peptides derived from CT7 which bind to an HLA molecule on the surface of a patient's tumor cells are administered to the patient, in an amount sufficient for the peptides to bind to the MHC/HLA molecules, and provoke lysis by T cells. Any combination of peptides may be used. These peptides, which may be used alone or in combination, as well as the entire protein or immunoreactive portions thereof, may be administered to a subject in need thereof, using any of the standard types of administration, such as intravenous, intradermal, subcutaneous, oral, rectal, and transdermal administration. Standard pharmaceutical carriers, adjuvants, such as saponins, GM-CSF, and interleukins and so forth may also be used. Further, these peptides and proteins may be formulated into vaccines with the listed material, as may dendritic cells, or other cells which present relevant MHC/peptide complexes.

Similarly, the invention contemplates therapies wherein nucleic acid molecules which encode CT-7, one or more or peptides which are derived from CT-7 are incorporated into a vector, such as a vaccinia or adenovirus based vector, to render it transfectable into eukaryotic cells, such as human cells. Similarly, nucleic acid molecules which encode one or more of the peptides may be incorporated into these vectors, which are then the major constituent of nucleic acid bases therapies.

Any of these assays can also be used in progression/regression studies. One can monitor the course of abnormality involving expression of CT-7 simply by monitoring levels of the protein, its expression, antibodies against it and so forth using any or all of the methods set forth supra.

It should be clear that these methodologies may also be used to track the efficacy of a therapeutic regime. Essentially, one can take a baseline value for the CT7 protein, using any of the assays discussed supra, administer a given therapeutic agent, and then monitor levels of the protein thereafter, observing changes in CT7 levels as indicia of the efficacy of the regime.

As was indicated supra, the invention involves, inter alia, the recognition of an "integrated" immune response to the CT7 molecule. One ramification of this is the ability to monitor the course of cancer therapy. In this method, which is a part of the invention, a subject in need of the therapy receives a vaccination of a type described herein. Such a vaccination results, e.g., in a T cell response against cells presenting HLA/peptide complexes on their cells. The response also includes an antibody response, possibly a result of the release of antibody provoking proteins via the lysis of cells by the T cells. Hence, one can monitor the effect of a vaccine, by monitoring an antibody response. As is indicated, supra, an increase in antibody titer may be taken as an indicia of progress with a vaccine, and vice versa.

Hence, a further aspect of the invention is a method for monitoring efficacy of a vaccine, following administration thereof, by determining levels of antibodies in the subject which are specific for the vaccine itself, or a large molecules of which the vaccine is a part.

The identification of CT7 proteins as being implicated in pathological conditions such as cancer also suggests a number of therapeutic approaches in addition to those discussed supra. The experiments set forth supra establish that antibodies are produced in response to expression of the protein. Hence, a further embodiment of the invention is the treatment of conditions which are characterized by aberrant or abnormal levels of CT-7 proteins, via administration of antibodies, such as humanized antibodies, antibody fragments, and so forth. These may be tagged or labelled with appropriate cystostatic or cytotoxic reagents.

T cells may also be administered. It is to be noted that the T cells may be elicited in vitro using immune responsive cells such as dendritic cells, lymphocytes, or any other immune responsive cells, and then reperfused into the subject being treated.

Note that the generation of T cells and/or antibodies can also be accomplished by administering cells, preferably treated to be rendered non-proliferative, which present relevant T cell or B cell epitopes for response, such as the epitopes discussed supra.

The therapeutic approaches may also include antisense therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the known BCG vaccine, and so forth.

Also apart of the inventions are peptides, such as those set forth in FIG. 1, and those which have as a core sequence

PQSPLQI (SEQ ID NO:3).

These peptides may be used therapeutically, via administration to a patient who expresses CT7 in connection with a pathology, as well as diagnostically. i.e., to determine if relevant antibodies are present and so forth.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. Isolated cancer associated antigen comprising the amino acid sequence encoded by nucleotides 287–3714 of SEQ ID NO: 1.

2. Immunogenic composition comprising the isolated antigen of claim 1, and a pharmaceutically acceptable adjuvant.

3. The immunogenic composition of claim 2, wherein said adjuvant is a cytokine, a saponin, or GM-CSF.

* * * * *

SEQUENCE LISTING

<160> NUMBER OF SEQ ID NOS: 8

<210> SEQ ID NO 1
<211> LENGTH: 4265
<212> TYPE: DNA
<213> ORGANISM: Homo sapiens
<220> FEATURE:

<400> SEQUENCE: 1

-continued

```
gtctgaagga cctgaggcat tttgtgacga ggatcgtctc aggtcagcgg agggaggaga      60
cttatagacc tatccagtct tcaaggtgct ccagaaagca ggagttgaag acctgggtgt     120
gagggacaca tacatcctaa aagcaccaca gcagaggagg cccaggcagt gccaggagtc     180
aaggttccca gaagacaaac cccctaggaa gacaggcgac ctgtgaggcc ctagagcacc     240
accttaagag aagaagagct gtaagccggc ctttgtcaga gccatcatgg gggacaagga     300
tatgcctact gctgggatgc cgagtcttct ccagagttcc tctgagagtc ctcagagttg     360
tcctgagggg gaggactccc agtctcctct ccagattccc cagagttctc ctgagagcga     420
cgacaccctg tatcctctcc agagtcctca gagtcgttct gagggggagg actcctcgga     480
tcctctccag agacctcctg aggggaagga ctcccagtct cctctccaga ttccccagag     540
ttctcctgag ggcgacgaca cccagtctcc tctccagaat tctcagagtt ctcctgaggg     600
gaaggactcc ctgtctcctc tagagatttc tcagagccct cctgagggtg aggatgtcca     660
gtctcctctg cagaatcctg cgagttcctt cttctcctct gctttattga gtatttttcca    720 gagttcccct gagagtattc aaagtccttt tgagggtttt ccccagtctg ttctccagat     780
tcctgtgagc gccgcctcct cctccacttt agtgagtatt ttcagagtt ccctgagag      840 tactcaaagt ccttttgagg gttttcccca gtctccactc cagattcctg tgagccgctc     900
cttctcctcc actttattga gtattttcca gagttcccct gagagaagtc agagaacttc     960
tgagggtttt gcacagtctc ctctccagat tcctgtgagc tcctcctcgt cctccacttt    1020
actgagtctt ttcagagttt ccctgagag aactcagagt acttttgagg gttttcccca    1080
gtctccactc cagattcctg tgagccgctc cttctcctcc actttattga gtattttcca    1140
gagttcccct gagagaactc agagtacttt tgagggtttt gcccagtctc ctctccagat    1200
tcctgtgagc ccctccttct cctccacttt agtgagtatt ttcagagtt ccctgagag     1260 aactcagagt acttttgagg gttttcccca gtctcctctc cagattcctg tgagctcctc    1320
cttctcctcc actttattga gtcttttcca gagttcccct gagagaactc agagtacttt    1380
tgagggtttt ccccagtctc ctctccagat tcctggaagc ccctccttct cctccacttt    1440
actgagtctt ttcagagtt ccctgagag aactcacagt acttttgagg gttttcccca    1500
gtctcctctc cagattccta tgacctcctc cttctcctct actttattga gtattttaca    1560
gagttctcct gagagtgctc aaagtgcttt tgagggtttt ccccagtctc ctctccagat    1620
tcctgtgagc tcctctttct cctacacttt attgagtctt ttcagagtt ccctgagag     1680 aactcacagt acttttgagg gttttcccca gtctcctctc cagattcctg tgagctcctc    1740
ctcctcctcc tccactttat tgagtctttt ccagagttcc cctgagtgta ctcaaagtac    1800
ttttgagggt ttccccagt ctcctctcca gattcctcag agtcctcctg aagggagaa    1860 tacccattct cctctccaga ttgttccaag tcttcctgag tgggaggact ccctgtctcc    1920
tcactacttt cctcagagcc ctcctcaggg ggaggactcc ctatctcctc actactttcc    1980
tcagagccct cctcaggggg aggactccct gtcctcac tactttcctc agagccctca    2040
gggggaggac tccctgtctc ctcactactt tcctcagagc cctcctcagg gggaggactc    2100
catgtctcct ctctactttc ctcagagtcc tcttcagggg gaggaattcc agtcttctct    2160
ccagagccct gtgagcatct gctcctcctc cactccatcc agtcttcccc agagtttccc    2220
tgagagttct cagagtcctc ctgagggggc tgtccagtct cctctccata gtcctcagag    2280
ccctcctgag gggatgcact cccaatcctcc tctcagagt cctgagagtg ctcctgaggg    2340
ggaggattcc ctgtctcctc tccaaattcc tcagagtcct cttgagggag aggactccct    2400
```

-continued

```
gtcttctctc cattttcctc agagtcctcc tgagtgggag gactccctct ctcctctcca    2460 cttttcctcag tttcctcctc aggggaggga cttccagtct tctctccaga gtcctgtgag   2520
tatctgctcc tcctccactt ctttgagtct tccccagagt ttccctgaga gtcctcagag    2580
tcctcctgag gggcctgctc agtctcctct ccagagacct gtcagctcct tcttctccta   2640
cactttagcg agtcttctcc aaagttccca tgagagtcct cagagtcctc ctgagggggcc  2700 tgcccagtct cctctccaga gtcctgtgag ctccttcccc tcctccactt catcgagtct   2760
ttcccagagt tctcctgtga gctccttccc ctcctccact tcatcgagtc tttccaagag   2820
ttcccctgag agtcctctcc agagtcctgt gatctccttc tcctcctcca cttcattgag   2880
cccattcagt gaagagtcca gcagcccagt agatgaatat acaagttcct cagacaccctt  2940 gctagagagt gattccttga cagacagcga gtccttgata gagagcgagc ccttgttcac   3000
ttatacactg gatgaaaagg tggacgagtt ggcgcggttt cttctcctca aatatcaagt   3060
gaagcagcct atcacaaagg cagagatgct gacgaatgtc atcagcaggt cacgggcta   3120 cttcctgtg atcttcagga aagcccgtga gttcatagag atactttttg gcatttccct   3180
gagagaagtg gaccctgatg actcctatgt ctttgtaaac acattagacc tcacctctga  3240 gggggtgtctg agtgatgagc agggcatgtc ccagaaccgc ctcctgattc ttattctgag  3300
tatcatcttc ataaagggca cctatgcctc tgaggaggtc atctgggatg tgctgagtgg  3360
aataggggtg cgtgctggga gggagcactt tgcctttggg gagcccaggg agctcctcac  3420
taaagtttgg gtgcaggaac attacctaga gtaccgggag gtgcccaact cttctcctcc  3480
tcgttacgaa ttcctgtggg gtccaagagc tcattcagaa gtcattaaga ggaaagtagt  3540
agagtttttg gccatgctaa agaataccgt ccctattacc tttccatcct cttacaagga  3600
tgctttgaaa gatgtggaag agagagccca ggccataatt gacaccacag atgattcgac  3660
tgccacagaa agtgcaagct ccagtgtcat gtcccccagc ttctcttctg agtgaagtct  3720
agggcagatt cttccctctg agtttgaagg gggcagtcga gtttctacgt ggtggagggc  3780
ctggttgagg ctggagagaa cacagtgcta tttgcatttc tgttccatat gggtagttat  3840 gggggtttacc tgttttactt ttgggtatttt ttcaaatgct tttcctatta ataacaggtt  3900
taaatagctt cagaatccta gtttatgcac atgagtcgca catgtattgc tgtttttctg  3960
gtttaagagt aacagtttga tattttgtaa aaacaaaaac acacccaaac acaccacatt  4020
gggaaaacct tctgcctcat tttgtgatgt gtcacaggtt aatgtggtgt tactgtagga  4080 atttttcttga aactgtgaag gaactctgca gttaaatagt ggaataaagt aaaggattgt  4140
taatgtttgc atttcctcag gtcctttagt ctgttgttct tgaaaactaa agatacatac  4200
ctggtttgct tggcttacgt aagaaagtcg aagaaagtaa actgtaataa ataaaagtgt  4260
cagtg                                                              4265
```

<210> SEQ ID NO 2
<211> LENGTH: 1142
<212> TYPE: PRT
<213> ORGANISM: Homo sapiens
<220> FEATURE:

<400> SEQUENCE: 2

Met Gly Asp Lys Asp Met Pro Thr Ala Gly Met Pro Ser Leu Leu Gln
              5                  10                  15

Ser Ser Ser Glu Ser Pro Gln Ser Cys Pro Glu Gly Glu Asp Ser Gln
          20                  25                  30

-continued

```
Ser Pro Leu Gln Ile Pro Gln Ser Ser Pro Glu Ser Asp Asp Thr Leu
         35                  40                  45
Tyr Pro Leu Gln Ser Pro Gln Ser Arg Ser Glu Gly Glu Asp Ser Ser
         50                  55                  60
Asp Pro Leu Gln Arg Pro Pro Glu Gly Lys Asp Ser Gln Ser Pro Leu
65                   70                  75                  80
Gln Ile Pro Gln Ser Ser Pro Glu Gly Asp Asp Thr Gln Ser Pro Leu
                 85                  90                  95
Gln Asn Ser Gln Ser Ser Pro Gly Lys Asp Ser Leu Ser Pro Leu
                 100                 105                 110
Glu Ile Ser Gln Ser Pro Pro Glu Gly Glu Asp Val Gln Ser Pro Leu
                 115                 120                 125
Gln Asn Pro Ala Ser Ser Phe Phe Ser Ser Ala Leu Leu Ser Ile Phe
         130                 135                 140
Gln Ser Ser Pro Glu Ser Ile Gln Ser Pro Phe Glu Gly Phe Pro Gln
145                 150                 155                 160
Ser Val Leu Gln Ile Pro Val Ser Ala Ala Ser Ser Ser Thr Leu Val
                 165                 170                 175
Ser Ile Phe Gln Ser Ser Pro Glu Ser Thr Gln Ser Pro Phe Glu Gly
                 180                 185                 190
Phe Pro Gln Ser Pro Leu Gln Ile Pro Val Ser Arg Ser Phe Ser Ser
             195                 200                 205
Thr Leu Leu Ser Ile Phe Gln Ser Ser Pro Glu Arg Ser Gln Arg Thr
         210                 215                 220
Ser Glu Gly Phe Ala Gln Ser Pro Leu Gln Ile Pro Val Ser Ser Ser
225                 230                 235                 240
Ser Ser Ser Thr Leu Leu Ser Leu Phe Gln Ser Ser Pro Glu Arg Thr
             245                 250                 255
Gln Ser Thr Phe Glu Gly Phe Pro Gln Ser Pro Leu Gln Ile Pro Val
             260                 265                 270
Ser Arg Ser Phe Ser Ser Thr Leu Leu Ser Ile Phe Gln Ser Ser Pro
         275                 280                 285
Glu Arg Thr Gln Ser Thr Phe Glu Gly Phe Ala Gln Ser Pro Leu Gln
         290                 295                 300
Ile Pro Val Ser Pro Ser Phe Ser Ser Thr Leu Val Ser Ile Phe Gln
305                 310                 315                 320
Ser Ser Pro Glu Arg Thr Gln Ser Thr Phe Glu Gly Phe Pro Gln Ser
             325                 330                 335
Pro Leu Gln Ile Pro Val Ser Ser Phe Ser Ser Thr Leu Leu Ser
             340                 345                 350
Leu Phe Gln Ser Ser Pro Glu Arg Thr Gln Ser Thr Phe Glu Gly Phe
         355                 360                 365
Pro Gln Ser Pro Leu Gln Ile Pro Gly Ser Pro Ser Phe Ser Ser Thr
         370                 375                 380
Leu Leu Ser Leu Phe Gln Ser Pro Glu Arg Thr His Ser Thr Phe
385                 390                 395                 400
Glu Gly Phe Pro Gln Ser Pro Leu Gln Ile Pro Met Thr Ser Ser Phe
             405                 410                 415
Ser Ser Thr Leu Leu Ser Ile Leu Gln Ser Ser Pro Glu Ser Ala Gln
             420                 425                 430
Ser Ala Phe Glu Gly Phe Pro Gln Ser Pro Leu Gln Ile Pro Val Ser
         435                 440                 445
```

```
Ser Ser Phe Ser Tyr Thr Leu Leu Ser Leu Phe Gln Ser Ser Pro Glu
    450                 455                 460

Arg Thr His Ser Thr Phe Glu Gly Phe Pro Gln Ser Pro Leu Gln Ile
465                 470                 475                 480

Pro Val Ser Ser Ser Ser Ser Ser Thr Leu Leu Ser Leu Phe Gln
                485                 490                 495

Ser Ser Pro Glu Cys Thr Gln Ser Thr Phe Glu Gly Phe Pro Gln Ser
            500                 505                 510

Pro Leu Gln Ile Pro Gln Ser Pro Glu Gly Glu Asn Thr His Ser
        515                 520                 525

Pro Leu Gln Ile Val Pro Ser Leu Pro Glu Trp Glu Asp Ser Leu Ser
        530                 535                 540

Pro His Tyr Phe Pro Gln Ser Pro Gln Gly Glu Asp Ser Leu Ser
545                 550                 555                 560

Pro His Tyr Phe Pro Gln Ser Pro Gln Gly Glu Asp Ser Leu Ser
                565                 570                 575

Pro His Tyr Phe Pro Gln Ser Pro Gln Gly Glu Asp Ser Leu Ser Pro
            580                 585                 590

His Tyr Phe Pro Gln Ser Pro Gln Gly Glu Asp Ser Met Ser Pro
        595                 600                 605

Leu Tyr Phe Pro Gln Ser Pro Leu Gln Gly Glu Glu Phe Gln Ser Ser
    610                 615                 620

Leu Gln Ser Pro Val Ser Ile Cys Ser Ser Thr Pro Ser Ser Leu
625                 630                 635                 640

Pro Gln Ser Phe Pro Glu Ser Ser Gln Ser Pro Pro Glu Gly Pro Val
                645                 650                 655

Gln Ser Pro Leu His Ser Pro Gln Ser Pro Pro Glu Gly Met His Ser
            660                 665                 670

Gln Ser Pro Leu Gln Ser Pro Glu Ser Ala Pro Glu Gly Glu Asp Ser
        675                 680                 685

Leu Ser Pro Leu Gln Ile Pro Gln Ser Pro Leu Glu Gly Glu Asp Ser
690                 695                 700

Leu Ser Ser Leu His Phe Pro Gln Ser Pro Pro Glu Trp Glu Asp Ser
705                 710                 715                 720

Leu Ser Pro Leu His Phe Pro Gln Phe Pro Pro Gln Gly Glu Asp Phe
                725                 730                 735

Gln Ser Ser Leu Gln Ser Pro Val Ser Ile Cys Ser Ser Ser Thr Ser
            740                 745                 750

Leu Ser Leu Pro Gln Ser Phe Pro Glu Ser Pro Gln Ser Pro Pro Glu
        755                 760                 765

Gly Pro Ala Gln Ser Pro Leu Gln Arg Pro Val Ser Ser Phe Phe Ser
770                 775                 780

Tyr Thr Leu Ala Ser Leu Leu Gln Ser Ser His Glu Ser Pro Gln Ser
785                 790                 795                 800

Pro Pro Glu Gly Pro Ala Gln Ser Pro Leu Gln Ser Pro Val Ser Ser
                805                 810                 815

Phe Pro Ser Ser Thr Ser Ser Ser Leu Ser Gln Ser Ser Pro Val Ser
            820                 825                 830

Ser Phe Pro Ser Ser Thr Ser Ser Ser Leu Ser Lys Ser Ser Pro Glu
        835                 840                 845

Ser Pro Leu Gln Ser Pro Val Ile Ser Phe Ser Ser Ser Thr Ser Leu
    850                 855                 860

Ser Pro Phe Ser Glu Glu Ser Ser Ser Pro Val Asp Glu Tyr Thr Ser
```

-continued

```
               865                 870                 875                 880

Ser Ser Asp Thr Leu Leu Glu Ser Asp Ser Leu Thr Asp Ser Glu Ser
                885                 890                 895

Leu Ile Glu Ser Glu Pro Leu Phe Thr Tyr Thr Leu Asp Glu Lys Val
                900                 905                 910

Asp Glu Leu Ala Arg Phe Leu Leu Lys Tyr Gln Val Lys Gln Pro
                915                 920                 925

Ile Thr Lys Ala Glu Met Leu Thr Asn Val Ile Ser Arg Tyr Thr Gly
        930                 935                 940

Tyr Phe Pro Val Ile Phe Arg Lys Ala Arg Glu Phe Ile Glu Ile Leu
945                 950                 955                 960

Phe Gly Ile Ser Leu Arg Glu Val Asp Pro Asp Ser Tyr Val Phe
                965                 970                 975

Val Asn Thr Leu Asp Leu Thr Ser Glu Gly Cys Leu Ser Asp Glu Gln
                980                 985                 990

Gly Met Ser Gln Asn Arg Leu Leu Ile Leu Ile Ser Ile Ile Phe
                995                 1000                1005

Ile Lys Gly Thr Tyr Ala Ser Glu Glu Val Ile Trp Asp Val Leu Ser
        1010                1015                1020

Gly Ile Gly Val Arg Ala Gly Arg Glu His Phe Ala Phe Gly Glu Pro
1025                1030                1035                1040

Arg Glu Leu Leu Thr Lys Val Trp Val Gln Glu His Tyr Leu Glu Tyr
                1045                1050                1055

Arg Glu Val Pro Asn Ser Ser Pro Arg Tyr Glu Phe Leu Trp Gly
                1060                1065                1070

Pro Arg Ala His Ser Glu Val Ile Lys Arg Lys Val Val Glu Phe Leu
        1075                1080                1085

Ala Met Leu Lys Asn Thr Val Pro Ile Thr Phe Pro Ser Ser Tyr Lys
        1090                1095                1100

Asp Ala Leu Lys Asp Val Glu Glu Arg Ala Gln Ala Ile Ile Asp Thr
1105                1110                1115                1120

Thr Asp Asp Ser Thr Ala Thr Glu Ser Ala Ser Ser Val Met Ser
                1125                1130                1135

Pro Ser Phe Ser Ser Glu
        1140
```

```
<210> SEQ ID NO 3
<211> LENGTH: 7
<212> TYPE: PRT
<213> ORGANISM: Homo sapiens
<220> FEATURE:

<400> SEQUENCE: 3

Pro Gln Ser Pro Leu Gln Ile
 1               5

<210> SEQ ID NO 4
<211> LENGTH: 4159
<212> TYPE: DNA
<213> ORGANISM: Homo sapiens
<220> FEATURE:

<400> SEQUENCE: 4
ggtggatgcg tttgggttgt agctaggctt tttcttttct ttctctttta aaacacatct      60
agacaaggaa aaaacaagcc tcggatctga tttttcactc ctcgttcttg tgcttggttc     120
ttactgtgtt tgtgtatttt aaaggcgaga agacgagggg aacaaaacca gctggatcca     180
```

-continued

```
tccatcaccg tgggtggttt taattttttcg ttttttctcg ttattttttt ttaaacaacc    240
actcttcaca atgaacaaac tgtatatcgg aaacctcagc gagaacgccg ccccctcgga    300
cctagaaagt atcttcaagg acgccaagat cccggtgtcg ggaccttcc tggtgaagac     360
tggctacgcg ttcgtggact gcccggacga gagctgggcc ctcaaggcca tcgaggcgct    420
ttcaggtaaa atagaactgc acgggaaacc catagaagtt gagcactcgg tcccaaaaag    480
gcaaaggatt cggaaacttc agatacgaaa tatcccgcct catttacagt gggaggtgct    540
ggatagttta ctagtccagt atggagtggt ggagagctgt gagcaagtga acactgactc    600
ggaaactgca gttgtaaatg taacctattc cagtaaggac caagctagac aagcactaga    660
caaactgaat ggatttcagt tagagaattt caccttgaaa gtagcctata tccctgatga    720
aatggccgcc cagcaaaacc ccttgcagca gccccgaggt cgccgggggc ttgggcagag    780
gggctcctca aggcagggt ctccaggatc cgtatccaag cagaaaccat gtgatttgcc     840
tctgcgcctg ctggttccca cccaatttgt tggagccatc ataggaaaag aaggtgccac    900
cattcggaac atcaccaaac agacccagtc taaaatcgat gtccaccgta aagaaaatgc    960
gggggctgct gagaagtcga ttactatcct ctctactcct gaaggcacct ctgcggcttg   1020
taagtctatt ctggagatta tgcataagga agctcaagat ataaaattca cagaagagat   1080
cccccttgaag attttagctc ataataactt tgttggacgt cttattggta agaaggaag   1140
aaatcttaaa aaaattgagc aagacacaga cactaaaatc acgatatctc cattgcagga   1200
attgacgctg tataatccag aacgcactat tacagttaaa ggcaatgttg agacatgtgc   1260
caaagctgag gaggagatca tgaagaaaat cagggagtct tatgaaaatg atattgcttc   1320
tatgaatctt caagcacatt taattcctgg attaaatctg aacgccttgg gtctgttccc   1380
acccacttca gggatgccac ctcccacctc agggcccct tcagccatga ctcctcccta    1440
cccgcagttt gagcaatcag aaacggagac tgttcatcag tttatcccag ctctatcagt   1500
cggtgccatc atcggcaagc agggccagca catcaagcag cttttctcgct ttgctggagc   1560
ttcaattaag attgctccag cggaagcacc agatgctaaa gtgaggatgg tgattatcac   1620
tggaccacca gaggctcagt tcaaggctca gggaagaatt tatggaaaaa ttaaagaaga   1680
aaactttgtt agtcctaaag aagaggtgaa acttgaagct catatcagag tgccatcctt   1740
tgctgctggc agagttattg gaaaggagg caaaacggtg aatgaacttc agaatttgtc    1800
aagtgcagaa gttgttgtcc ctcgtgacca gacacctgat gagaatgacc aagtggttgt   1860
caaaataact ggtcacttct atgcttgcca ggttgcccag agaaaaattc aggaaattct   1920
gactcaggta aagcagcacc aacaacagaa ggctctgcaa agtggaccac ctcagtcaag   1980
acggaagtaa aggctcagga aacagcccac cacagaggca gatgccaaac caaagacaga   2040
ttgcttaacc aacagatggg cgctgacccc ctatccagaa tcacatgcac aagttttac    2100
ctagccagtt gtttctgagg accaggcaac ttttgaactc ctgtctctgt gagaatgtat   2160
actttatgct ctctgaaatg tatgacaccc agctttaaaa caaacaaaca aacaaacaaa   2220
aaaagggtgg gggagggagg gaaagagaag agctctgcac ttccctttgt tgtagtctca   2280
cagtataaca gatattctaa ttcttcttaa tattcccca taatgccaga aattggctta    2340
atgatgcttt cactaaattc atcaaataga ttgctcctaa atccaattgt taaaattgga   2400
tcagaataat tatcacagga acttaaatgt taagccatta gcatagaaaa actgttctca   2460
gttttatttt tacctaacac taacatgagt aacctaaggg aagtgctgaa tggtgttggc   2520
```

```
agggtatta aacgtgcatt tttactcaac tacctcaggt attcagtaat acaatgaaaa    2580
gcaaaattgt tccttttttt tgaaaatttt atatacttta taatgataga agtccaaccg    2640 tttttaaaa aataaattta aaatttaaca gcaatcagct aacaggcaaa ttaagatttt     2700
tacttctggc tggtgacagt aaagctggaa aattaatttc agggtttttt gaggcttttg    2760
acacagttat tagttaaatc aaatgttcaa aaatacggag cagtgcctag tatctggaga    2820
gcagcactac catttattct ttcatttata gttgggaaag ttttttgacgg tactaacaaa   2880 gtggtcgcag gagattttgg aacggctggt ttaaatggct tcaggagact tcagtttttt    2940
gtttagctac atgattgaat gcataataaa tgctttgtgc ttctgactat caatacctaa    3000
agaaagtgca tcagtgaaga gatgcaagac tttcaactga ctggcaaaaa gcaagcttta    3060
gcttgtctta taggatgctt agtttgccac tacacttcag accaatggga cagtcataga    3120
tggtgtgaca gtgtttaaac gcaacaaaag gctacatttc catggggcca gcactgtcat    3180
gagcctcact aagctatttt gaagattttt aagcactgat aaattaaaaa aaaaaaaaaa    3240
aaattagact ccaccttaag tagtaaagta taacaggatt tctgtatact gtgcaatcag    3300
ttctttgaaa aaaaagtcaa aagatagaga atacaagaaa agttttnggg atataatttg    3360
aatgactgtg aaaacatatg acctttgata acgaactcat ttgctcactc cttgacagca    3420
aagcccagta cgtacaattg tgttgggtgt gggtggtctc caaggccacg ctgctctctg    3480
aattgatttt ttgagttttg gnttgnaaga tgatcacagn catgttacac tgatcttnaa    3540
ggacatatnt tataaccctt taaaaaaaaa atccctgcc tcattcttat ttcgagatga     3600
atttcgatac agactagatg tctttctgaa gatcaattag acattntgaa aatgatttaa    3660
agtgttttcc ttaatgttct ctgaaaacaa gtttcttttg tagttttaac caaaaaagtg    3720 cccttttgt cactggtttc tcctagcatt catgattttt ttttcacaca atgaattaaa     3780
attgctaaaa tcatggactg gctttctggt tggatttcag gtaagatgtg tttaaggcca    3840
gagcttttct cagtatttga ttttttttccc caatatttga ttttttaaaa atatacacat   3900
aggagctgca tttaaaacct gctggtttaa attctgtcan atttcacttc tagccttta    3960 gtatggcnaa tcanaattta cttttactta agcatttgta atttggagta tctggtacta    4020
gctaagaaat aattcnataa ttgagttttg tactcnccaa anatgggtca ttcctcatgn    4080
ataatgtncc cccaatgcag cttcatttc caganaacctt gacgcaggat aaattttttc    4140
atcatttagg tccccaaaa                                                4159
```

<210> SEQ ID NO 5
<211> LENGTH: 1708
<212> TYPE: DNA
<213> ORGANISM: Homo sapiens
<220> FEATURE:

<400> SEQUENCE: 5

```
agggacgctg ccgcaccgcc ccagtttacc ccggggagcc atcatgaagc tgaatggcca      60
ccagttggag aaccatgccc tgaaggtctc ctacatcccc gatgagcaga tagcacaggg    120
acctgagaat gggcgccgag ggggctttgg ctctcggggt cagccccgcc agggctcacc    180
tgtggcagcg ggggccccag ccaagcagca gcaagtggca tccccttc ggctcctggt      240 gcccacccag tatgtgggtg ccattattgg caaggagggg gccaccatcc gcaacatcac    300
aaaacagacc cagtccaaga tagacgtgca taggaaggag aacgcaggtg cagctgaaaa    360
agccatcagt gtgcactcca cccctgaggg ctgctcctcc gcttgtaaga tgatcttgga    420
```

-continued

```
gattatgcat aaagaggcta aggacaccaa aacggctgac gaggttcccc tgaagatcct      480
ggcccataat aactttgtag ggcgtctcat tggcaaggaa ggacggaacc tgaagaaggt      540
agagcaagat accgagacaa aaatcaccat ctcctcgttg caagacctta ccctttacaa      600
ccctgagagg accatcactg tgaaggggc catcgagaat tgttgcaggg ccgagcagga       660
aataatgaag aaagttcggg aggcctatga gaatgatgtg gctgccatga gctctcacct      720
gatccctggc ctgaacctgg ctgctgtagg tctttttccca gcttcatcca gcgcagtccc    780
gccgcctccc agcagcgtta ctggggctgc tccctatagc tcctttatgc aggctcccga     840
gcaggagatg gtgcaggtgt ttatccccgc ccaggcagtg ggcgccatca tcggcaagaa     900
ggggcagcac atcaaacagc tctcccggtt tgccagcgcc tccatcaaga ttgcaccacc     960
cgaaacacct gactccaaag ttcgtatggt tatcatcact ggaccgccag aggcccaatt    1020
caaggctcag ggaagaatct atggcaaact caaggaggag aacttctttg gtcccaagga    1080
ggaagtgaag ctggagaccc acatacgtgt gccagcatca gcagctggcc gggtcattgg    1140
caaaggtgga aaacggtga acgagttgca gaatttgacg gcagctgagg tggtagtacc     1200
aagagaccag accccctgatg agaacgacca ggtcatcgtg aaaatcatcg acatttcta    1260
tgccagtcag atggctcaac ggaagatccg agacatcctg gcccaggtta agcagcagca    1320
tcagaaggga cagagtaacc aggcccaggc acggaggaag tgaccagccc ctccctgtcc    1380
cttngagtcc aggacaacaa cgggcagaaa tcgagagtgt gctctcccg gcaggcctga    1440
gaatgagtgg gaatccggga cacntgggcc gggctgtaga tcaggtttgc ccacttgatt    1500
gagaaagatg ttccagtgag gaaccctgat ctntcagccc caaacaccca cccaattggc    1560
ccaacactgt ntgcccctcg gggtgtcaga aattntagcg caaggcactt ttaaacgtgg    1620
attgttttaaa gaagctctcc aggccccacc aagagggtgg atcacacctc agtgggaaga   1680
aaaataaaat ttccttcagg ttttaaaa                                       1708

<210> SEQ ID NO 6
<211> LENGTH: 3412
<212> TYPE: DNA
<213> ORGANISM: Homo sapiens
<220> FEATURE:

<400> SEQUENCE: 6
ggcagcggag gaggcgagga gcgccgggta ccgggccggg ggagccgcgg gctctcgggg      60
aagagacgga tgatgaacaa gctttacatc gggaacctga gccccgccgt caccgccgac    120
gacctccggc agctctttgg ggacaggaag ctgcccctgg cgggacaggt cctgctgaag    180
tccggctacg ccttcgtgga ctaccccgac cagaactggg ccatccgcgc catcgagacc    240
ctctcgggta aagtggaatt gcatgggaaa atcatggaag ttgattactc agtctctaaa    300
aagctaagga gcaggaaaat tcagattcga aacatccctc ctcacctgca gtgggaggtg    360
ttggatggac ttttggctca atatgggaca gtggagaatg tggaacaagt caacacagac    420
acagaaaccg ccgttgtcaa cgtcacatat gcaacaagaa agaagcaaa atagccatg      480
gagaagctaa gcgggcatca gtttgagaac tactccttca gatttcctta catcccggat    540
gaagaggtga gctccccttc gcccctcag cgagcccagc gtgggacca ctcttccccg      600
gagcaaggcc acgccctggg ggcacttct caggccagac agattgattt ccgctgcgg      660
atcctggtcc ccacccagtt tgttggtgcc atcatcggaa aggaggcctt gaccataaag    720
aacatcacta agcagaccca gtcccgggta gatatccata gaaaagagaa ctctggagct    780
```

-continued

```
gcagagaagc ctgtcaccat ccatgccacc ccagagggga cttctgaagc atgccgcatg      840
attcttgaaa tcatgcagaa agaggcagat gagaccaaac tagccgaaga gattcctctg      900
aaaatcttgg cacacaatgg cttggttgga agactgattg aaaagaagg cagaaatttg       960 aagaaaattg aacatgaaac agggaccaag ataacaatct catctttgca ggatttgagc      1020
atatacaacc cggaaagaac catcactgtg aagggcacag ttgaggcctg tgccagtgct      1080
gagatagaga ttatgaagaa gctgcgtgag gcctttgaaa atgatatgct ggctgttaac      1140
caacaagcca atctgatccc agggttgaac ctcagcgcac ttggcatctt ttcaacagga      1200
ctgtccgtgc tatctccacc agcagggccc cgcggagctc cccccgctgc ccctaccac       1260 cccttcacta cccactccgg atacttctcc agcctgtacc cccatcacca gtttggcccg      1320
ttcccgcatc atcactctta tccagagcag gagattgtga atctcttcat cccaacccag      1380
gctgtgggcg ccatcatcgg gaagaagggg gcacacatca aacagctggc gagattcgcc      1440
ggagcctcta tcaagattgc ccctgcggaa ggcccagacg tcagcgaaag gatggtcatc      1500
atcaccgggc caccggaagc ccagttcaag gcccagggac ggatctttgg gaaactgaaa      1560
gaggaaaact tctttaaccc caaagaagaa gtgaagctgg aagcgcatat cagagtgccc      1620
tcttccacag ctggccgggt gattggcaaa gtggcaaga ccgtgaacga actgcagaac       1680
ttaaccagtg cagaagtcat cgtgcctcgt gaccaaacgc cagatgaaaa tgaggaagtg      1740
atcgtcagaa ttatcgggca cttctttgct agccagactg cacagcgcaa gatcagggaa      1800
attgtacaac aggtgaagca gcaggagcag aaataccctc agggagtcgc ctcacagcgc      1860
agcaagtgag gctcccacag gcaccagcaa acaacggat gaatgtagcc cttccaacac       1920
ctgacagaat gagaccaaac gcagccagcc agatcgggga caaccaaag accatctgag      1980 gaatgagaag tctgcggagg cggccaggga ctctgccgag gccctgagaa ccccaggggc      2040
cgaggagggg cggggaaggt cagccaggtt tgccagaacc accgagcccc gcctcccgcc      2100
ccccagggct tctgcaggct tcagccatcc acttcaccat ccactcggat ctctcctgaa      2160
ctcccacgac gctatccctt ttagttgaac taacataggt gaacgtgttc aaagccaagc      2220
aaaatgcaca cccttttttct gtggcaaatc gtctctgtac atgtgtgtac atattagaaa     2280
gggaagatgt taagatatgt ggcctgtggg ttacacaggg tgcctgcagc ggtaatatat      2340
tttagaaata atatatcaaa taactcaact aactccaatt tttaatcaat tattaatttt     2400
tttttctttt taaagagaaa gcaggctttt ctagactttta aagaataaag tctttgggag    2460
gtctcacggt gtagagagga gctttgaggc caccgcaca aaattcaccc agagggaaat       2520
ctcgtcggaa ggacactcac ggcagttctg gatcacctgt gtatgtcaac agaagggata     2580
ccgtctcctt gaagaggaaa ctctgtcact cctcatgcct gtctagctca tacacccatt     2640
tctctttgct tcacaggttt taaactggtt ttttgcatac tgctatataa ttctctgtct     2700
ctctctgttt atctctcccc tccctcccct cccttcttc tccatctcca ttcttttgaa      2760
tttcctcatc cctccatctc aatcccgtat ctacgcaccc ccccccccc aggcaaagca      2820 gtgctctgag tatcacatca cacaaaagga acaaaagcga aacacacaaa ccagcctcaa      2880
cttacacttg gttactcaaa agaacaagag tcaatggtac ttgtcctagc gttttggaag     2940
aggaaaacag gaacccacca aaccaaccaa tcaaccaaac aaagaaaaaa ttccacaatg     3000
aaagaatgta ttttgtcttt ttgcattttg gtgtataagc catcaatatt cagcaaaatg     3060
attcctttct ttaaaaaaaa aaatgtggag gaaagtagaa atttaccaag gttgttggcc     3120
cagggcgtta aattcacaga ttttttttaac gagaaaaaca cacagaagaa gctacctcag   3180
```

| | |
|---|---|
| gtgtttttac ctcagcacct tgctcttgtg tttcccttag agattttgta aagctgatag | 3240 |
| ttggagcatt ttttattttt tttaataaaa atgagttgga aaaaaaataa gatatcaact | 3300 |
| gccagcctgg agaaggtgac agtccaagtg tgcaacagct gttctgaatt gtcttccgct | 3360 |
| agccaagaac cnatatggcc ttcttttgga caaaccttga aaatgtttat tt | 3412 |

<210> SEQ ID NO 7
<211> LENGTH: 1946
<212> TYPE: DNA
<213> ORGANISM: Homo sapiens
<220> FEATURE:

<400> SEQUENCE: 7

| | |
|---|---|
| gctgtagcgg aggggctggg gggctgctct gtccccttcc ttgcgcgctg cggcctcagc | 60 |
| ccacccagag gccggggtgg gagggcgagt gctcagcttc ccgggttagg agccggaaaa | 120 |
| ttcaaatccg aaatattcca ccccagctcc gatgggaagt actggacagc ctgctggctc | 180 |
| agtatggtac agtagagaac tgtgagcaag tgaacaccga gagtgagacg gcagtggtga | 240 |
| atgtcaccta ttccaaccgg gagcagacca ggcaagccat catgaagctg aatggccacc | 300 |
| agttggagaa ccatgccctg aaggtctcct acatccccga tgagcagata gcacagggac | 360 |
| ctgagaatgg gcgccgaggg ggctttggct ctcgggtca gccccgccag ggctcacctg | 420 |
| tggcagcggg ggccccagcc aagcagcagc aagtggacat ccccccttcgg ctcctggtgc | 480 |
| ccacccagta tgtgggtgcc attattggca aggaggggc caccatccgc aacatcacaa | 540 |
| aacagaccca gtccaagata gacgtgcata ggaaggagaa cgcaggtgca gctgaaaaag | 600 |
| ccatcagtgt gcactccacc cctgagggct gctcctccgc ttgtaagatg atcttggaga | 660 |
| ttatgcataa agaggctaag gacaccaaaa cggctgacga ggttcccctg aagatcctgg | 720 |
| cccataataa ctttgtaggg cgtctcattg caaggaagg acggaacctg aagaaggtag | 780 |
| agcaagatac cgagacaaaa atcaccatct cctcgttgca agaccttacc ctttacaacc | 840 |
| ctgagaggac catcactgtg aagggggcca tcgagaattg ttgcagggcc gagcaggaaa | 900 |
| taatgaagaa agttcgggag gcctatgaga atgatgtggc tgccatgagc tctcacctga | 960 |
| tccctggcct gaacctggct gctgtaggtc ttttcccagc ttcatccagc gcagtcccgc | 1020 |
| cgcctcccag cagcgttact ggggctgctc cctatagctc ctttatgcag gctcccgagc | 1080 |
| aggagatggt gcaggtgttt atccccgccc aggcagtggg cgccatcatc ggcaagaagg | 1140 |
| ggcagcacat caaacagctc tcccggtttg ccagcgcctc catcaagatt gcaccacccg | 1200 |
| aaacacctga ctccaaagtt cgtatggtta tcatcactgg accgccagag gcccaattca | 1260 |
| aggctcaggg aagaatctat ggcaaactca aggaggagaa cttctttggt cccaaggagg | 1320 |
| aagtgaagct ggagacccac atacgtgtgc cagcatcagc agctggccgg gtcattggca | 1380 |
| aaggtggaaa aacggtgaac gagttgcaga atttgacggc agctgaggtg gtagtaccaa | 1440 |
| gagaccagac ccctgatgag aacgaccagg tcatcgtgaa aatcatcgga catttctatg | 1500 |
| ccagtcagat ggctcaacgg aagatccgag acatcctggc ccaggttaag cagcagcatc | 1560 |
| agaagggaca gagtaaccag gcccaggcac ggaggaagtg accagcccct ccctgtccct | 1620 |
| tngagtccag gacaacaacg ggcagaaatc gagagtgtgc tctccccggc aggcctgaga | 1680 |
| atgagtggga atccgggaca cntgggccgg gctgtagatc aggtttgccc acttgattga | 1740 |
| gaaagatgtt ccagtgagga accctgatct ntcagcccca aacacccacc caattggccc | 1800 |
| aacactgtnt gccctcgggg gtgtcagaaa ttntagcgca aggcactttt aaacgtggat | 1860 |

-continued tgtttaaaga agctctccag gccccaccaa gagggtggat cacacctcag tgggaagaaa      1920
aataaaattt ccttcaggtt ttaaaa                                           1946

<210> SEQ ID NO 8
<211> LENGTH: 3283
<212> TYPE: DNA
<213> ORGANISM: Homo sapiens
<220> FEATURE:

<400> SEQUENCE: 8
ggcagcggag gaggcgagga gcgccgggta ccgggccggg ggagccgcgg gctctcgggg      60
aagagacgga tgatgaacaa gctttacatc gggaacctga gccccgccgt caccgccgac     120
gacctccggc agctctttgg ggacaggaag ctgcccctgg cgggacaggt cctgctgaag     180
tccggctacg ccttcgtgga ctaccccgac cagaactggg ccatccgcgc catcgagacc     240
ctctcgggta aagtggaatt gcatgggaaa atcatggaag ttgattactc agtctctaaa     300
aagctaagga gcaggaaaat tcagattcga aacatccctc ctcacctgca gtgggaggtg     360
ttggatggac ttttggctca atatgggaca gtggagaatg tggaacaagt caacacagac     420
acagaaaccg ccgttgtcaa cgtcacatat gcaacaagag aagaagcaaa aatagccatg     480
gagaagctaa gcgggcatca gtttgagaac tactccttca agatttccta catcccggat     540
gaagaggtga gctccccttc gccccctcag cgagcccagc gtggggacca ctcttcccgg     600
gagcaaggcc acgcccctgg gggcacttct caggccagac agattgattt cccgctgcgg     660
atcctggtcc ccacccagtt tgttggtgcc atcatcggaa aggagggctt gaccataaag     720
aacatcacta agcagaccca gtcccgggta gatatccata gaaaagagaa ctctggagct     780
gcagagaagc ctgtcaccat ccatgccacc ccagagggga cttctgaagc atgccgcatg     840
attcttgaaa tcatgcagaa agaggcagat gagaccaaac tagccgaaga gattcctctg     900
aaaatcttgg cacacaatgg cttggttgga agactgattg aaaagaagg cagaaatttg     960 aagaaaattg aacatgaaac agggaccaag ataacaatct catctttgca ggatttgagc     1020
atatacaacc cggaaagaac catcactgtg aagggcacag ttgaggcctg tgccagtgct     1080
gagatagaga ttatgaagaa gctgcgtgag gcctttgaaa atgatatgct ggctgttaac     1140
acccactccg gatacttctc cagcctgtac ccccatcacc agtttggccc gttcccgcat     1200
catcactctt atccagagca ggagattgtg aatctcttca tcccaaccca ggctgtgggc     1260
gccatcatcg ggaagaaggg ggcacacatc aaacagctgg cgagattcgc cggagcctct     1320
atcaagattg cccctgcgga aggcccagac gtcagcgaaa ggatggtcat catcaccggg     1380
ccaccggaag cccagttcaa ggcccaggga cggatctttg ggaaactgaa agaggaaaac     1440
ttctttaacc ccaaagaaga agtgaagctg aagcgcata tcagagtgcc ctcttccaca     1500
gctggccggg tgattggcaa aggtggcaag accgtgaacg aactgcagaa cttaaccagt     1560
gcagaagtca tcgtgcctcg tgaccaaacg ccagatgaaa atgaggaagt gatcgtcaga     1620
attatcgggc acttctttgc tagccagact gcacagcgca agatcaggga aattgtacaa     1680
caggtgaagc agcaggagca gaaataccct cagggagtcg cctcacagcg cagcaagtga     1740
ggctcccaca ggcaccagca aaacaacgga tgaatgtagc ccttccaaca cctgacagaa     1800
tgagaccaaa cgcagccagc cagatcggga gcaaaccaaa gaccatctga ggaatgagaa     1860
gtctgcggag gcggccaggg actctgccga ggccctgaga accccagggg ccgagggggg     1920
gcggggaagg tcagccaggt ttgccagaac caccgagccc gcctcccgc ccccagggc      1980

```
ttctgcaggc ttcagccatc cacttcacca tccactcgga tctctcctga actcccacga    2040
cgctatccct tttagttgaa ctaacatagg tgaacgtgtt caaagccaag caaaatgcac    2100 acccttttc  tgtggcaaat cgtctctgta catgtgtgta catattagaa agggaagatg    2160
ttaagatatg tggcctgtgg gttacacagg gtgcctgcag cggtaatata ttttagaaat    2220
aatatatcaa ataactcaac taactccaat ttttaatcaa ttattaattt ttttttcttt    2280
ttaaagagaa agcaggcttt tctagacttt aaagaataaa gtctttggga ggtctcacgg    2340
tgtagagagg agctttgagg ccacccgcac aaaattcacc cagagggaaa tctcgtcgga    2400
aggacactca cggcagttct ggatcacctg tgtatgtcaa cagaagggat accgtctcct    2460
tgaagaggaa actctgtcac tcctcatgcc tgtctagctc atacacccat ttctctttgc    2520
ttcacaggtt ttaaactggt tttttgcata ctgctatata attctctgtc tctctctgtt    2580
tatctctccc ctccctcccc tcccttcctt ctccatctcc attcttttga atttcctcat    2640
ccctccatct caatcccgta tctacgcacc ccccccccc  caggcaaagc agtgctctga    2700
gtatcacatc acacaaaagg aacaaaagcg aaacacacaa accagcctca acttacactt    2760
ggttactcaa aagaacaaga gtcaatggta cttgtcctag cgttttggaa gaggaaaaca    2820
ggaacccacc aaaccaacca atcaaccaaa caaagaaaaa attccacaat gaaagaatgt    2880
attttgtctt tttgcatttt ggtgtataag ccatcaatat tcagcaaaat gattcctttc    2940
tttaaaaaaa aaaatgtgga ggaaagtaga aatttaccaa ggttgttggc ccagggcgtt    3000
aaattcacag attttttaa  cgagaaaaac acacagaaga agctacctca ggtgttttta    3060
cctcagcacc ttgctcttgt gtttccctta gagattttgt aaagctgata gttggagcat    3120
ttttttattt ttttaataaa aatgagttgg aaaaaaaata agatatcaac tgccagcctg    3180
gagaaggtga cagtccaagt gtgcaacagc tgttctgaat tgtcttccgc tagccaagaa    3240
ccnatatggc cttcttttgg acaaaccttg aaaatgttta ttt                     3283
```